United States Patent
Yamamoto et al.

(10) Patent No.: US 6,963,394 B2
(45) Date of Patent: Nov. 8, 2005

(54) INSPECTING DEVICE FOR SEMICONDUCTOR WAFER

(75) Inventors: Takayasu Yamamoto, Aichi (JP); Tatefumi Oda, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 10/721,381

(22) Filed: Nov. 26, 2003

(65) Prior Publication Data

US 2004/0150814 A1 Aug. 5, 2004

(30) Foreign Application Priority Data

Nov. 29, 2002 (JP) .................................... P2002-346797

(51) Int. Cl.[7] .............................................. G01N 21/00
(52) U.S. Cl. ................ 356/237.4; 356/394; 250/559.29
(58) Field of Search .................... 356/237.1–237.6, 356/392–394, 614–615, 621–624, 399–401; 250/559.29, 559.3, 559.36, 559.4, 548; 414/936, 331, 783

(56) References Cited

U.S. PATENT DOCUMENTS

| | | | | |
|---|---|---|---|---|
| 4,887,904 A | * | 12/1989 | Nakazato et al. | 356/621 |
| 5,194,743 A | * | 3/1993 | Aoyama et al. | 250/548 |
| 5,258,823 A | * | 11/1993 | Akamatsu | 356/615 |
| 5,740,034 A | * | 4/1998 | Saeki | 700/59 |
| 5,851,102 A | * | 12/1998 | Okawa et al. | 414/783 |
| 6,201,603 B1 | * | 3/2001 | Miura | 356/615 |
| 6,222,624 B1 | | 4/2001 | Yonezawa | |
| 6,399,957 B1 | * | 6/2002 | Murata | 250/559.4 |
| 6,549,290 B2 | * | 4/2003 | Miura et al. | 356/614 |

FOREIGN PATENT DOCUMENTS

| | | |
|---|---|---|
| JP | 4-128605 A | 4/1992 |
| JP | 9-186290 A | 7/1997 |
| JP | 11-194098 A | 7/1999 |

* cited by examiner

Primary Examiner—Gregory J. Toatley, Jr.
Assistant Examiner—Sang H. Nguyen
(74) Attorney, Agent, or Firm—Sughrue Mion, PLLC

(57) ABSTRACT

A inspecting device for a semiconductor wafer comprises: a holding unit which holds a wafer; an aligner unit which detects a cutout position and a center position of the wafer held by the holding unit and obtains position determining data of the wafer; an observing unit for magnifying and observing fine patterns on the wafer, the observing unit being disposed at a position where the wafer held by the holding unit can be observed; a moving unit which relatively moves the holding unit with respect to the observing unit; and a control unit which controls the moving unit to move the holding unit based on the obtained position data so that the fine patterns at a desired position can be observed.

4 Claims, 8 Drawing Sheets

90

90'

INSPECTING DEVICE FOR SEMICONDUCTOR WAFER

BACKGROUND OF THE INVENTION

The present invention relates to an inspecting device for inspecting a semiconductor wafer.

In an inspecting device for inspecting a semiconductor wafer with a microscope so as to check and inspect fine patterns formed on a surface of the semiconductor wafer, positioning of the wafer is important. Therefore, or a cutout portion, which is referred to as a notch or an orientation flat, is formed on an edge portion of the wafer so that the notch or the orientation flat can be used as a reference of positioning the wafer. As a method of detecting the notch or the orientation flat and also detecting a central position of the wafer, a method is provided in which a set of a detecting unit composed of an illuminating light source and a light receiving element is arranged so that an edge portion of the wafer can be interposed between the illuminating light source and the light receiving element and information on a profile of the wafer edge can be obtained by a change in shading signals provided by the detecting unit.

However, the positioning mechanism of positioning the wafer and the inspecting mechanism of checking and inspecting fine patterns with a microscope are composed different from each other. Therefore, it is necessary to provide a conveyance mechanism of conveying the wafer from the positioning mechanism to the inspecting mechanism. Accordingly, the size of the device is increased. Further, it is difficult to reduce the inspection process time.

SUMMARY OF THE INVENTION

The present invention has been accomplished in view of the above conventional problems. It is a technical task of the present invention to provide an inspecting device for a semiconductor wafer, the structure of which is simple so that the inspection process time can be reduced.

In order to solve the aforesaid object, the invention is characterized by having the following arrangement.

(1) A inspecting device for a semiconductor wafer comprising:
a holding unit which holds a wafer;
an aligner unit which detects a cutout position and a center position of the wafer held by the holding unit and obtains position determining data of the wafer;
an observing unit for magnifying and observing fine patterns on the wafer, the observing unit being disposed at a position where the wafer held by the holding unit can be observed;
a moving unit which relatively moves the holding unit with respect to the observing unit; and
a control unit which controls the moving unit to move the holding unit based on the obtained position data so that the fine patterns at a desired position can be observed.

(2) The inspecting device according to (1), wherein the moving unit includes:
a rotating unit which relatively rotates the holding unit with respect to the observing unit; and
a horizontally moving unit which relatively moves the holding unit with respect to the observing unit in a substantially horizontally direction.

(3) The inspecting device according to (1), wherein
the moving unit includes a rotating unit which relatively rotates the holding unit with respect to the aligner unit, and
the control unit controls the rotating unit to rotating the holding unit every predetermined angle and detects the cutout position and the center position with the aligner unit by obtaining distances from a rotational center to an edge of the wafer at each predetermined angle.

(4) The inspecting device according to (1), wherein
the observing unit includes a photograph unit which captures an image of the fine pattern on the wafer, and
the control unit control the moving unit to move the holding unit based on the image captured by the photograph unit.

(5) The inspecting device according to (1), wherein
the observing unit includes a photograph unit which captures an image of the fine pattern on the wafer, and
the inspecting device further comprises a computing unit which judges if the wafer is proper based on the image captured by the photograph unit.

(6) A inspecting device for a semiconductor wafer comprising:
a holding unit which holds the wafer;
an aligner unit which detects a cutout position and a center position of the wafer held by the holding unit;
an observing unit for magnifying and observing fine patterns on the wafer, the observing unit being disposed at a position where the wafer held by the holding unit can be observed;
a rotating unit which relatively rotates the holding unit with respect to the aligner unit and the observing unit;
a horizontally moving unit which relatively moves the holding unit with respect to the observing unit in a substantially horizontally direction; and
a control unit which controls the rotating unit to rotate the holding unit every predetermined angle, detects the cutout position and the center position with the aligner unit by obtaining distances from a rotational center to an edge of the wafer at each predetermined angle, and controls the rotating unit and the horizontally moving unit to move the holding unit based on the obtained position data so that the fine patterns at a desired position can be observed.

DETAILED DESCRIPTION OF PREFERRED EMBODIMENTS

Figure 1:
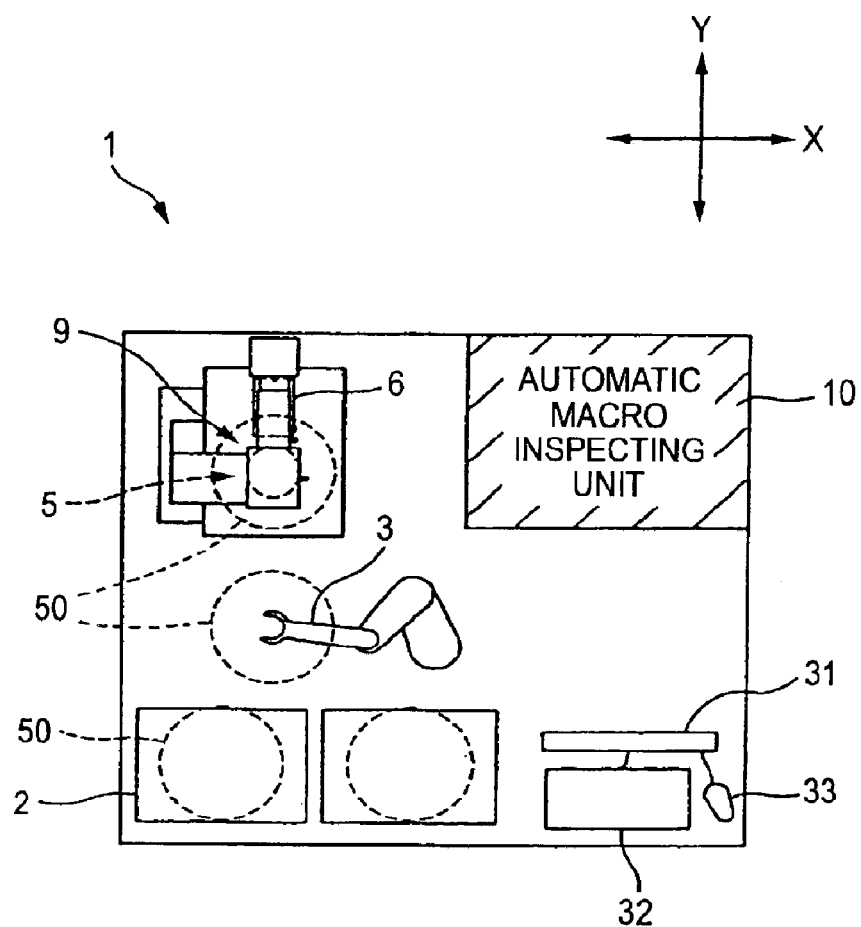
FIG. 1 is a plan view showing an outline of the structure of a semiconductor wafer inspecting device.

Referring to the drawings, an embodiment of the present invention will be explained below. FIG. 1 is a plan view showing an outline of the structure of an inspecting device 1 for inspecting a semiconductor wafer of the embodiment.

Reference numeral 2 is a carrier for accommodating the wafers 50. Reference numeral 5 is a stage unit for holding, rotating and moving the wafer 50 in the directions X and Y (in the substantially horizontal direction). Reference numeral 6 is an aligner unit for detecting the position of the cutout portion (a notch or an orientation flat) and the central position of the wafer 50. Reference unit 9 is a microscope unit for magnifying and observing the wafer 50 and is arranged at a position where the microscope unit 9 can observes the wafer 50 held by the stage unit 5. Reference numeral 3 is a robot arm for conveying the wafer 50 among the carrier 2, the stage unit 5 and the automatic macro inspecting unit 10. Incidentally, the robot arm 3 and the stage unit 5 suck and hold the wafer 50 by the action of vacuum generated by a vacuum source such as a vacuum pump not shown in the drawing. Reference numeral 31 is a monitor for displaying a result of the inspection. Reference numeral 32 is a keyboard and reference numeral 33 is a mouse, which are used when the inspecting conditions and others are inputted.

Figure 2:
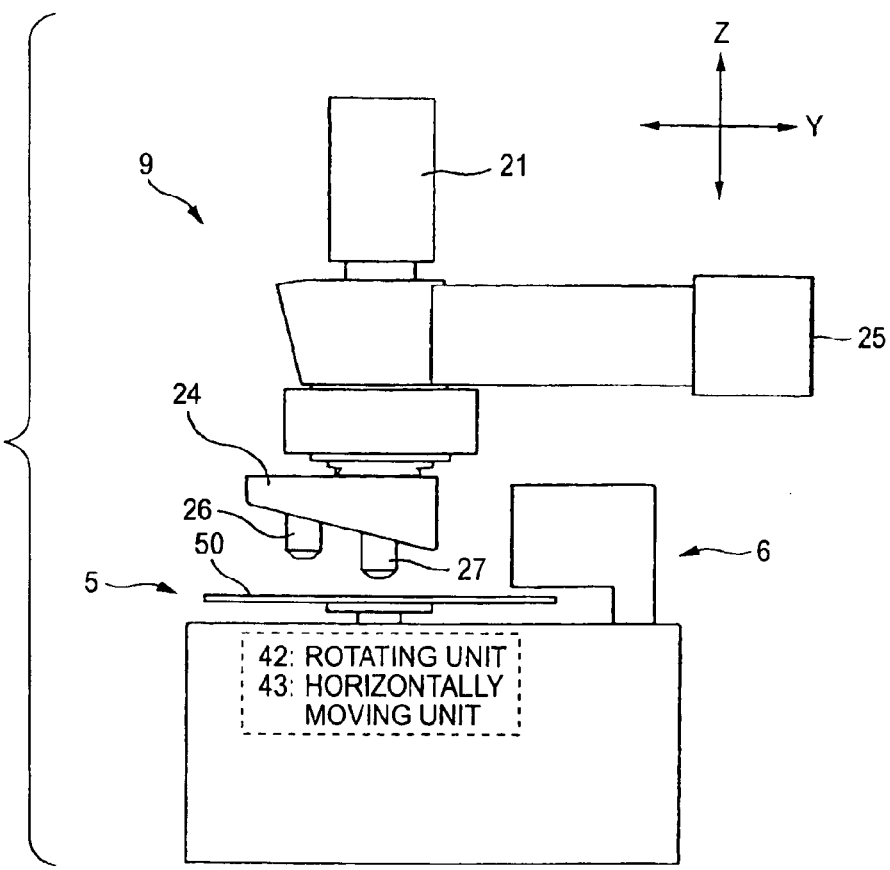
FIG. 2 is a side view showing an outline of the structure of a stage unit, an aligner unit and a microscope unit.
Figure 3A:
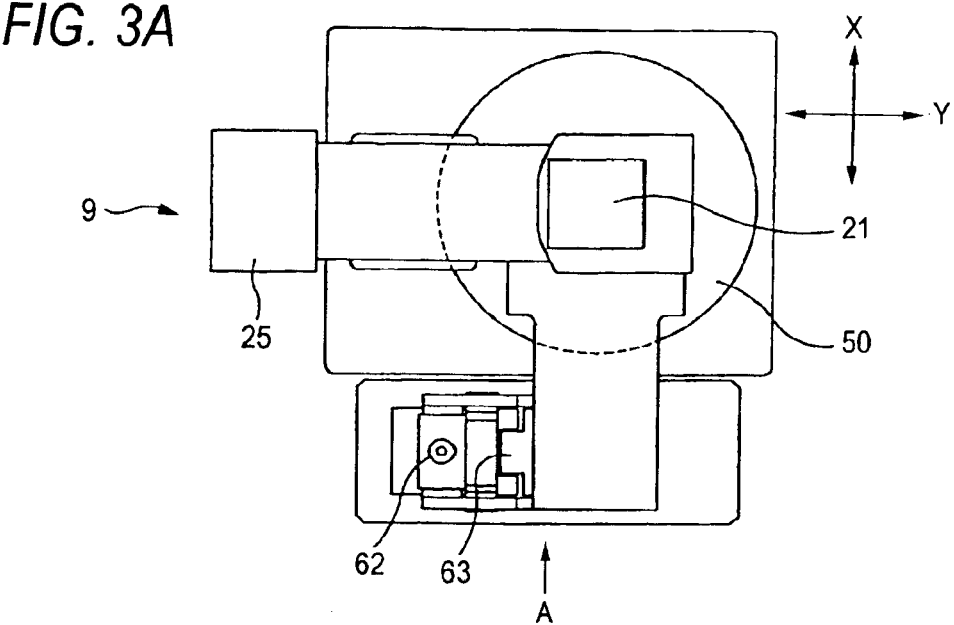
FIGS. 3A and 3B are a plan view and side view showing an outline of the structure of the stage unit, the aligner unit and the microscope unit.
Figure 3B:
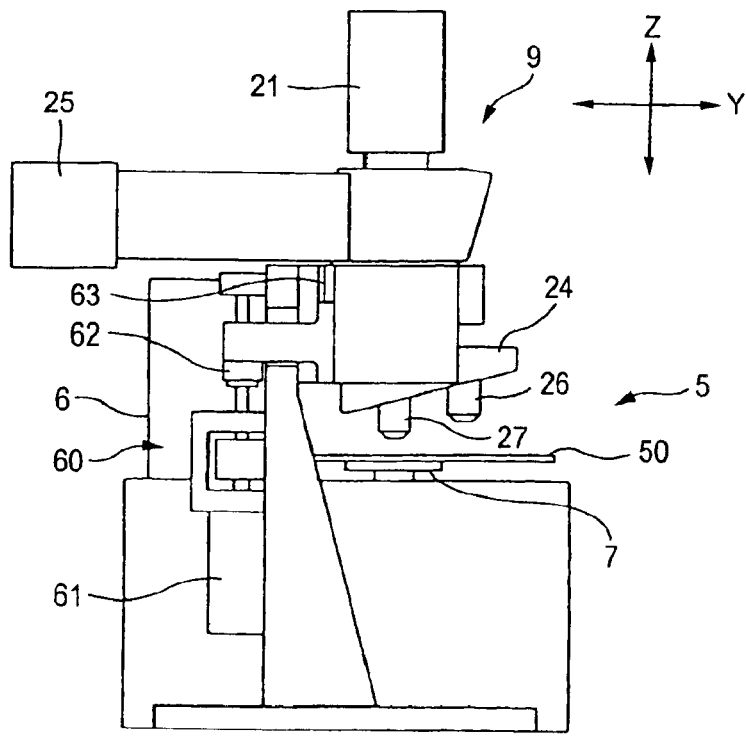

FIG. 2 is a side view showing an outline of the structure of the stage unit 5, the aligner unit 6 and the microscope unit 9. FIG. 3A is a plan view showing an outline of the structure of these components. FIG. 3B is a side view taken in the direction of arrow A in FIG. 3A.

The microscope unit 9 is constituted in such a manner that the lamp 25 illuminates a surface of the wafer 50 to be inspected and a camera 21 captures fine patterns formed on the surface of the wafer 50 to be inspected. The fine patterns are magnified by objective lenses 26, 27. The magnification of the objective lens 26 is 2.5 times, and the magnification of the objective lens 27 is 20 times. According to the desired magnification, the objective lenses 26, 27 are changed over by the revolution of an electrical revolver 24. Further, the microscope unit 9 is moved in the direction Z (the substantially vertical direction) by a vertically moving unit 60 so that an image to be captured can be focused. This vertically moving unit 60 is provided with a rail 63 for guiding the microscope unit 9 in the direction Z by a ball screw 62 for converting the rotation of a motor 61 into a linear movement.

The stage unit 5 is provided with a mounting table 7 for holding the wafer 50, a horizontally moving unit 43 and a rotating unit 42. In the same manner as to the vertical moving unit 60, the horizontally moving unit 43 is provided with not shown a motor, a ball screw and a rail for moving in the X and Y directions and moves the mounting table 7 in the X and Y directions. Therefore, the rotating unit 42 is provided with a not shown motor and rotates the mounting table 7.

Figure 4A:
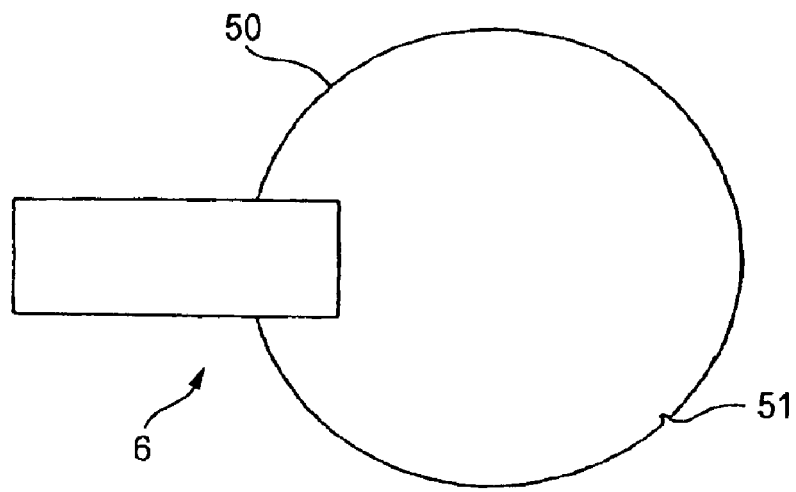
FIGS. 4A and 4B are views showing an outline of the structure of the aligner unit.
Figure 4B:
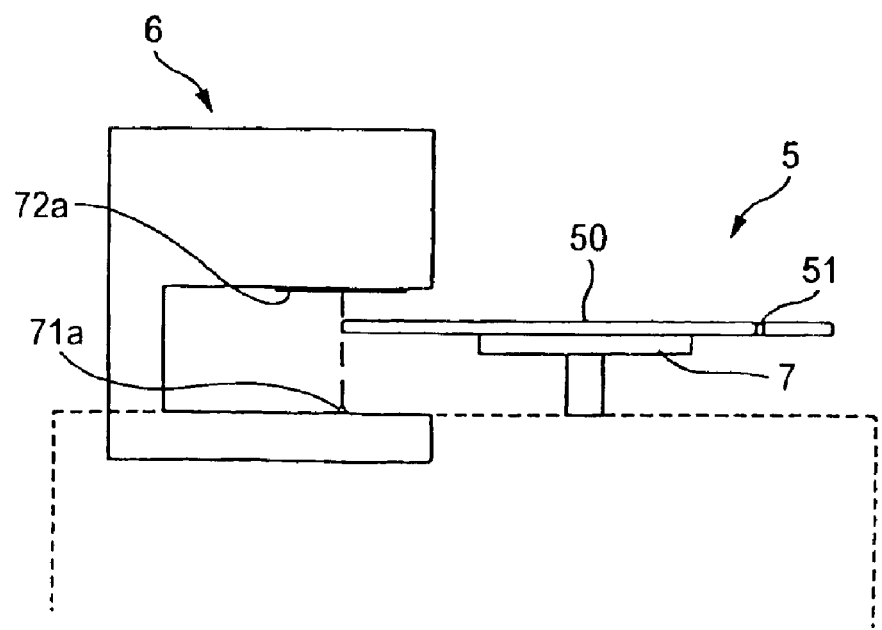

FIGS. 4A and 4B are views showing an outline of the structure of the aligner unit 6. Specifically, FIG. 4A is a plan view of the aligner unit 6 and the wafer 50. FIG. 4B is a side view of the aligner unit 6 and the wafer 50. Reference numeral 51 is a notch (a cutout portion) of the wafer 50. The aligner unit 6 includes: an LED (light source) 71*a* for emitting light for detection toward an edge portion of the wafer 50; and a light receiving element 72*a* such as a line sensor for receiving the light for detection.

Figure 5:
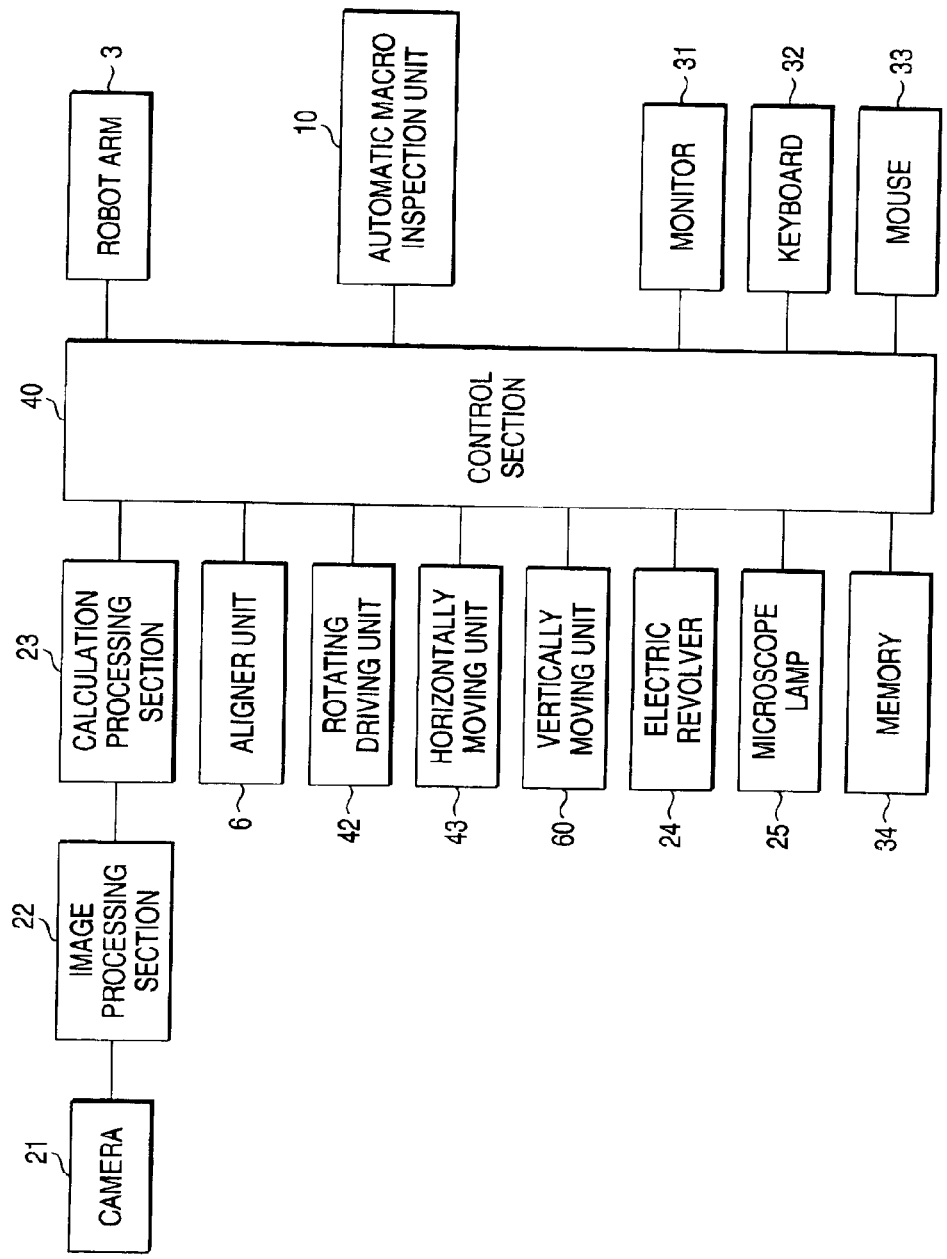
FIG. 5 is a block diagram showing a control system of the wafer inspecting device.
Figure 6:
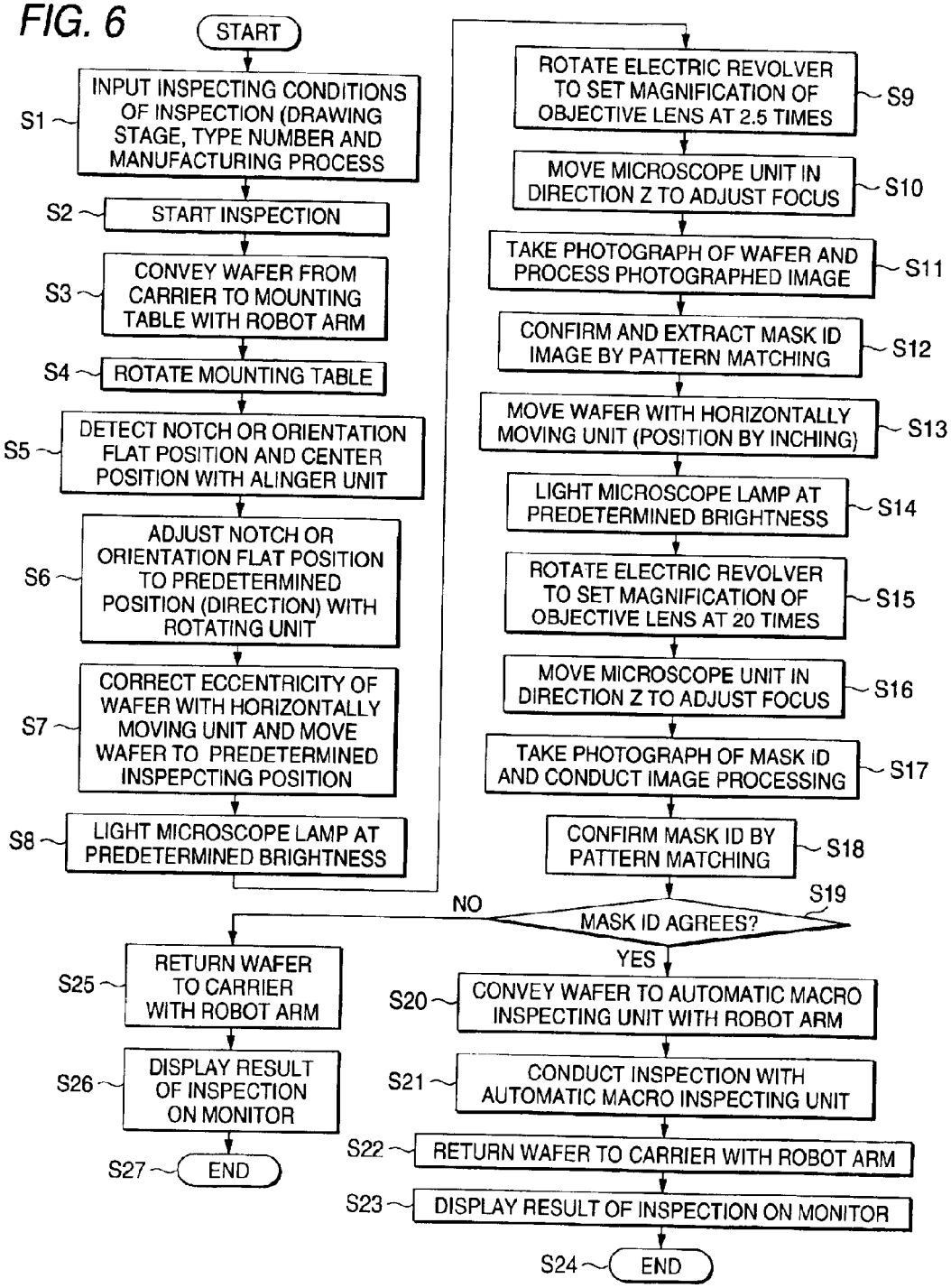
FIG. 6 is a view showing a flow chart.

Operation conducted in the device composed as described above will be explained referring to the control system block diagram shown in FIG. 5 and the flow chart shown in FIG. 6.

First, while watching the monitor 31, an operator operates the keyboard 32 and the mouse 33 to designate and input the inspecting conditions such as a stage of the carrier 2 from which the wafer 50 is drawn out, a number showing the type of a pattern of IC or memory and a manufacturing process.

Next, when the operator inputs a command of the start of inspection with the keyboard 32 or the mouse 33, a control section 40 drives the robot arm 3, sucks and hold the wafer 50 from the designated stage of the carrier 2, and conveys the wafer 50 to the mounting table 7 of the stage unit 5. After the wafer 50 is placed and sucked onto the mounting table 7, the control section 40 drives the rotating unit 42 and rotates the mounting table 7. After the start of rotation, the control section 40 makes the aligner unit 6 detect the notch 51. By the beam light for detection from the LED 71*a*, a shade of the edge of the wafer 50 is projected to the light receiving element 72*a* attached to an upper portion with respect to the wafer 50. Each time the mounting table 7 is rotated a predetermined angle by the rotating unit 42, the control section 40 obtains a distance of the edge from the rotational center by a signal sent from the light receiving element 72*a*, and the thus obtained data is stored in the memory 34. After distance data corresponding to one rotation of the mounting table 7 has been obtained, the control section 40 read out the distance data stored in the memory and obtains a position of the rotational angle at which the distance is greatly change as the position of the notch 51. The control section 40 obtains a position of the center of the wafer 50 placed on the mounting table 7 from the distance data at each rotational angle.

Next, based on the obtained positioning data (rotational angle position data and central position data), the control section 40 controls the drive of the rotating unit 42 and the horizontally moving unit 43. That is, the control section 40 controls the rotating unit 42 to rotate the mounting table 7 so that the notch 51 of the wafer 50 can be positioned at a predetermined position (direction). While consideration is being given to the eccentricity of the central position from the rotational center, the control section 40 controls to move the mounting table 7 in the directions of X and Y by the horizontally moving unit 43 so that the wafer 50 can be positioned at a predetermined observing position.

The control section 40 controls the lamp 25 so that the lamp 25 can be lit by predetermined brightness. Then, the control section 40 controls the electric revolver 24 so that the objective lens 26, the magnification of which is 2.5 times, can be positioned on an optical axis of observation of the microscope unit 9 (camera 21).

Figure 7:
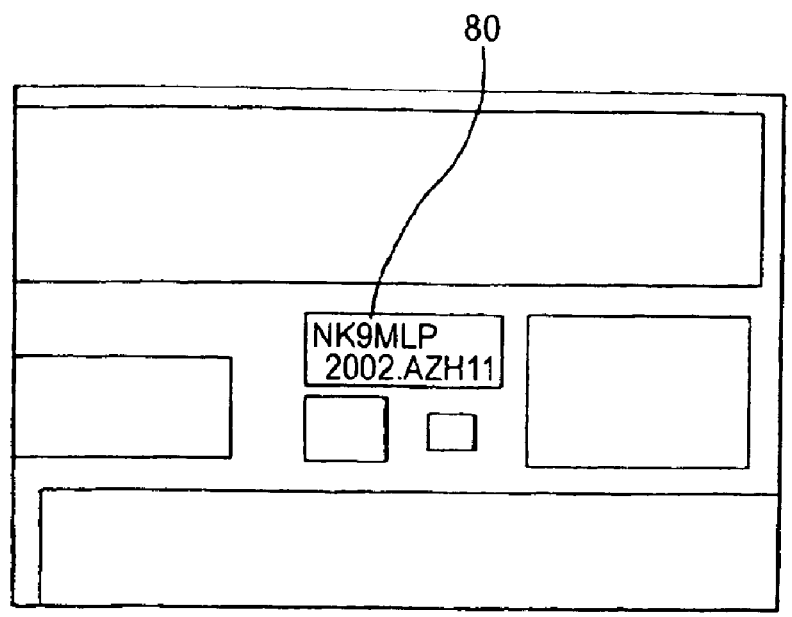
FIG. 7 is a view showing a mask ID.

Since the wafer 50 is positioned at a predetermined observing position by the rotating unit 42 and the horizontally moving unit 43, as shown by the example shown in FIG. 7, an observation image captured by the camera 21 includes a mask ID 80 showing a block copy number of the block copy used for pattern printing at the stepper in the semiconductor wafer manufacturing process. The observation image is processed by the image processing section 22. Since image data to be used as a reference of the mask ID 80 is previously stored in the memory 34, the calculation processing section 23 specifies and extracts the same image data as the stored image data by means of pattern matching from the processed image data to confirm the mask ID 80. In the case where the position of the mask ID 80 deviates from the center of the image plane, the mounting table 7 is moved by a very small distance in the directions X and Y by the horizontally moving unit 43.

Figure 8:
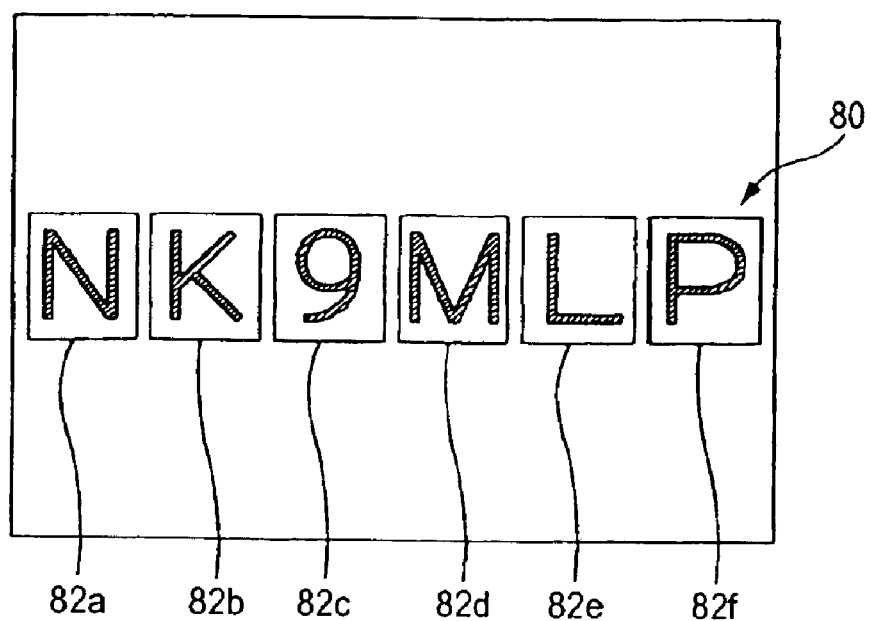
FIG. 8 is a view showing the mask ID.

Next, the control section 40 controls so that the lamp 25 can be lit at predetermined brightness, and the objective lens 27, the magnification of which is 20 times is positioned on the optical axis of observation of the microscope unit 9 (camera 21) by rotating the electric revolver 24. As shown in the example illustrated in FIG. 8, this observation image contains the mask ID 80 which has been magnified. In the same manner as that of the observation image, the magnification of which is 2.5 times, the observation image, the magnification of which is 20 times, is processed by the image processing section 22. Since image data, which becomes an individual reference, such as English letters and numerals identifying the mask ID 80 is previously stored in the memory 34, the calculation processing section 23 specifies and extracts the same data as the stored image data by means of pattern matching from the processed image data to judge whether or not the number of the mask ID 80 is appropriate.

In the case where the mask ID does not agree, the control section 40 controls the robot arm 3 so that the wafer 50 returns to the carrier 2, and it is displayed on the monitor 31 that the mask ID does not agree so as to inform the operator of the fact that the mask ID does not agree. In the case where the mask ID agrees, the control section 40 controls the robot arm 3 so that the robot arm 3 conveys the water 50 to the automatic macro inspecting unit 10. When the robot arm 3 receives the wafer 50 from the mounting table 7, the eccentricity of the wafer 50 is corrected by the rotating unit 42 and the horizontally moving unit 43. Further, the notch 51 is placed so that it can be directed in a predetermined direction.

The automatic macro inspecting unit 10 captures images of a plurality of fine patterns formed on a surface of the wafer 50 to be inspected and automatically conducts a macro inspection on the water 50 according to the thus captured image. Concerning the detail of the automatic macro inspecting unit, refer to JP-A-11-194098 (U.S. Pat. No. 6,222,624). After the completion of inspection conducted by the automatic macro inspecting unit 10, the control section 40 controls the robot arm 3 so that the robot arm 3 returns the wafer 50 to the carrier 2, and the result of inspection conducted by the macro inspecting unit 10 is displayed on the monitor 31.

While the macro inspecting unit 10 is conducting the inspection, the control section 40 controls the robot arm 3 so that the robot arm 3 takes out the next wafer from the carrier 2, and the wafer is positioned by the aligner unit 6 in the same manner as that described above and then the mask ID is confirmed. Whereby, after the previous wafer has been inspected by the macro inspecting unit 10, the next water is immediately supplied to the macro inspecting unit 10. Therefore, the throughput of inspection can be increased.

Figure 9A:
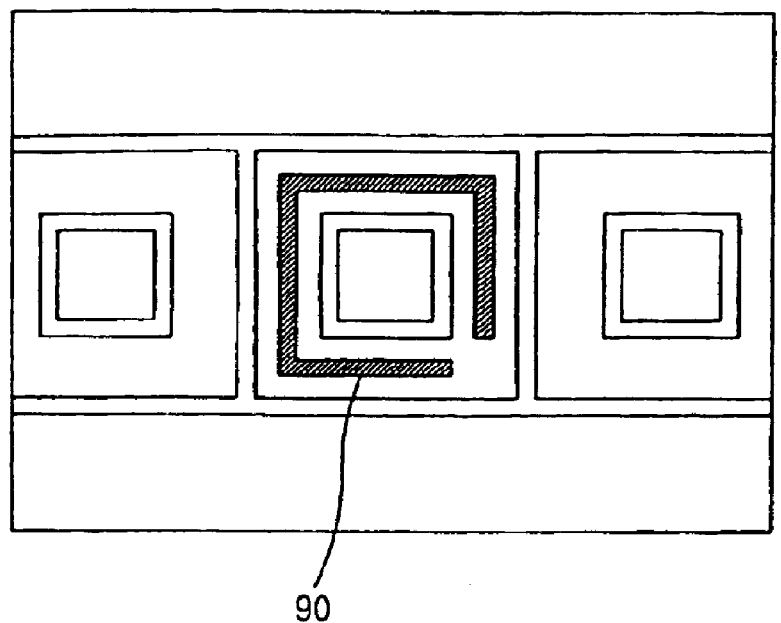
FIGS. 9A and 9B are views for explaining the shift of a pattern.
Figure 9B:
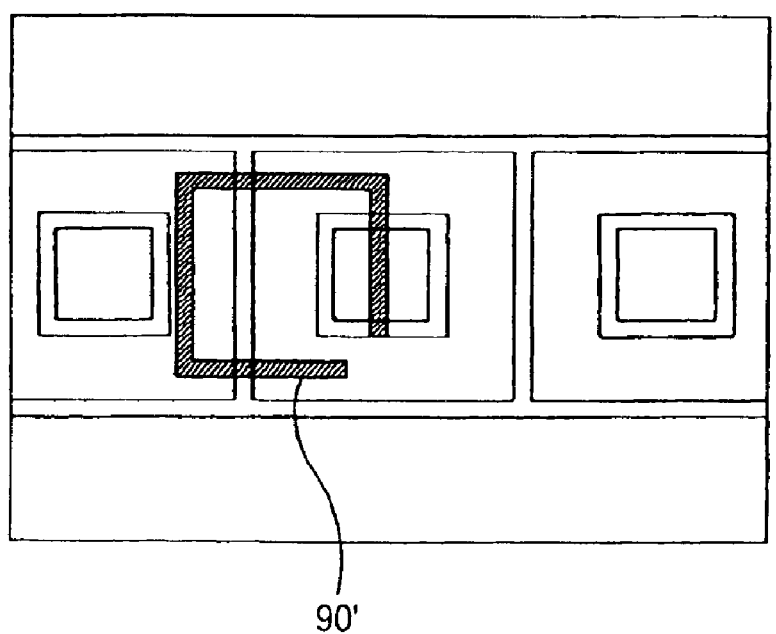

Incidentally, in the above embodiment, the mask ID is confirmed by the microscope unit 9. However, it should be noted that the present invention is not limited to the confirmation of the mask ID but the other fine patterns on the wafer may be inspected and confirmed. For example, as shown in FIG. 9A, the shaft of a pattern 90 may be confirmed by image processing with the microscope unit 9. For example, in the case where an image of the pattern 90', the position of which is shifted as shown in FIG. 9B, is captured, the wafer may be judged to be rejected.

In the above embodiment, after positioning of the wafer and the confirmation of the mask ID have been conducted by the aligner unit 6 and others, automatic macro inspection is conducted by the automatic macro inspecting unit 10. However, the present invention is not limited to the automatic macro inspection. The present invention may be applied to the other inspections.

As described above, according to the present invention, when the mechanism of positioning a wafer and the mechanism of checking and inspecting fine patterns with a microscope are integrated into one body, the constitution can be simplified and the inspecting process time can be shortened.

What is claimed is:

1. An inspecting device for a semiconductor wafer comprising:
    a holding unit which holds a wafer;
    a rotating unit which rotates the wafer by rotating the holding unit;
    an aligner unit which optically detects a cutout position and a center position of the wafer rotated by the rotating unit and obtains position determining data of the wafer;
    an observing unit for magnifying and observing fine patterns on the wafer, wherein the observing unit includes a camera portion for photoelectrical capture and is disposed at a position where the wafer held by the holding unit can be observed;
    a moving unit which relatively moves the holding unit with respect to the observing unit in an X-Y direction so as to keep a plane of the wafer at a same level;
    a control unit which controls the moving unit and the rotating unit to move and rotate the holding unit so as to position a mask ID of the wafer at a predetermined position within an observation field of the observing unit based on the obtained position determining data; and
    judging means for judging whether the mask ID of the wafer is appropriate by comparing image data which is photoelectrically captured by the camera portion and processed with stored reference image data of a mask ID.

2. The inspecting device according to claim 1 further comprising a macro inspection device, wherein when the mask ID of the wafer is appropriate, the wafer is transferred to the macro inspection device by a robot arm.

3. An inspecting device for a semiconductor wafer comprising:
    a holding unit which holds a wafer;
    a rotating unit which rotates the wafer by rotating the holding unit;
    an aligner unit which optically detects a cutout position and a center position of the wafer rotated by the rotating unit and obtains position determining data of the wafer;
    an observing unit for magnifying and observing fine patterns on the wafer, wherein the observing unit includes a camera portion for photoelectrical capture and is disposed at a position where the wafer held by the holding unit can be observed;
    a moving unit which relatively moves the holding unit with respect to the observing unit in an X-Y direction so as to keep a plane of the wafer at a same level;
    a control unit which controls the moving unit and the rotating unit to move and rotate the holding unit so as to position the fine pattern of the wafer at a predetermined position within an observation field of the observing unit based on the obtained position determining data; and
    judging means for judging whether the fine pattern of the wafer is appropriate by comparing image data which is photoelectrically captured by the camera portion and processed with stored reference image data of a fine pattern.

4. An inspecting device for a semiconductor wafer comprising:
    a holding unit which holds a wafer;
    a rotating unit which rotates the wafer by rotating the holding unit;

an aligner unit which optically detects a cutout position and a center position of the wafer rotated by the rotating unit and obtains position determining data of the wafer;

an observing unit for magnifying and observing fine patterns on the wafer, wherein the observing unit includes a camera portion for photoelectrical capture and is disposed at a position where the wafer held by the holding unit can be observed;

a moving unit which relatively moves the holding unit with respect to the observing unit in an X-Y direction so as to keep a plane of the wafer at a same level;

a control unit which controls the moving unit and the rotating unit to move and rotate the holding unit so as to position the fine pattern of the wafer at a predetermined position within an observation field of the observing unit based on the obtained position determining data; and a machine executable algorithm that judges whether the fine pattern of the wafer is appropriate by comparing image data which is photoelectrically captured by the camera portion and processed with stored reference image data of a fine pattern.

* * * * *